United States Patent [19]

Mitrani

[11] Patent Number: 5,387,576
[45] Date of Patent: Feb. 7, 1995

[54] TREATMENT OF HYPERPROLIFERATIVE EPIDERMAL CONDITIONS WITH ACTIVIN A

[75] Inventor: Eduardo Mitrani, Jerusalem, Israel

[73] Assignee: Yissum Research Development Co., Jerusalem, Israel

[21] Appl. No.: 967,262

[22] Filed: Oct. 27, 1992

[30] Foreign Application Priority Data

Oct. 27, 1991 [IL] Israel .......................... 99867

[51] Int. Cl.$^6$ .............. C07K 15/00; A01N 37/00
[52] U.S. Cl. ............................................. 514/2; 514/8; 514/12; 514/886; 514/887; 530/350
[58] Field of Search ................. 530/350; 435/65.4; 514/2, 8, 12, 882, 887

[56] References Cited

U.S. PATENT DOCUMENTS 4,798,885  1/1989  Mason et al. ................. 530/350

FOREIGN PATENT DOCUMENTS 0222491  5/1987  European Pat. Off. .

OTHER PUBLICATIONS

Korotkii et al. 1985 Vestn. Dermatol. Venerol. 0(7):48–51.

Bowman & Rand 1980, Textbook of Pharmacology 2nd Blackwell Scientific Publications Oxford, Selected pages.

Choi, Y., et al., "TGF–Beta and retinoic acid: regulators of growth and modifiers of differentiation in human epidermal cells", *Cell Regulation*, 1:791–809 (1990).

Lyons, K., et al., "Vgr–1, a mammalian gene related to Xenopus Vg–1, is a member of the transforming growth factor Beta gene superfamily", *Proc. Natl. Acad. Sci. USA*, 86:4554–4558 (1989).

Bullough W.S., et al., "The control of epidermal mitotic activity in the mouse", *Proc. Roy. Soc. B.*, 151:517–536 (1959).

Bichel, P. "Tumor Growth Inhibiting Effect of JP–I Ascitic Fluid–I" *Europ. J. Cancer* 6:291–296 (1970).

Albano, R. M., et al., "mesoderm–inducing factor produced by WEHI–3 murine myelomonocytic leukemia cells is activin A", *Development*, 110:435–443 (1990).

Ausubel, et al. "In Situ Hybridization and Immunohistochemistry" *Current Protocols in Molecular Biology.*

Schubert, D., et al., "Activin is a nerve cell survival molecule" *Nature*, 344:868–870 (1990).

Green, H., "The Keratinocyte as differentiation cell type", *The Harvey Lectures, Series 74*, 101–139, (1979).

Dvir, A., et al., "The Inhibition of EGF–dependent Proliferation of Keratinocytes by Tyrphostin Tyrosine Kinase Blockers" *The J. of Cell Biol.*, (113):857–865 (1991).

Smith, J. C., et al., "Identification of a potent Xenopus mesoderm–inducing factor as a homologue of activin A", *Nature*, 345:729–731 (1990).

Asashima, M., et al., "Mesodermal induction in early amphibian embryos by activin A (erythroid differentiation factor)", *Roux's Arch. Dev. Biol.* (198):330–335 (1990).

Mason, A. J., et al., "Complementary DNA sequences of ovarian follicular fluid inhibin show precursor structure and homology with transforming growth factor–beta", *Nature*, (318):659–663 (1985).

Ling, Nicholas, et al. "Pituitary FSH is released by a heterodimer of the Beta–subunits from the two forms of inhibin", *Nature*, (321):779–782 (1986).

Vale, W., et al., "Purification and characterization of an FSH releasing protein from porcine ovarian follicular fluid" *Nature*, (321):776–779 (1986).

Thomsen, G., et al., "Activins Are Expressed Early in Xenopus Embryogenesis and Can Induce Axial Mo- (List continued on next page.)

*Primary Examiner*—Garnette D. Draper
*Assistant Examiner*—K. Cochrane Carlson
*Attorney, Agent, or Firm*—Hamilton, Brook, Smith & Reynolds

[57] ABSTRACT

Pharmaceutical preparations for the treatment of hyperproliferative epidermal conditions comprising the specific negative growth factor activin A, and their use in methods of treatment of hyperproliferative epidermal conditions.

6 Claims, 3 Drawing Sheets

OTHER PUBLICATIONS esoderm and Anterior Structures", *Cell*, (63):485–493 (1990).

Jones, C. M., et al., "Involvement of Bone Morphogenetic Protein-4 (BMP-4) and Vgr-1 in morphogenesis and neurogenesis in the mouse" *Development*, 111:531–542 (1991).

Mitrani, E., et al., "Induction by Soluble Factors of Organized Axial Structures in Chick Epiblasts", *Science*, 247:1092–1094 (1990).

Mitrani, E., et al., "Activin Can Induce the Formation of Axial Structures and Is Expressed in the Hypoblast of the Chick", *Cell* 63-495–501 (1990).

Bichel, P., "Specific Growth Regulation in Three Ascitic Tumours" *Europ. J. Cancer*, 8:167–173 (1972).

Fearon E. R., et al., "A Genetic Model for Colorectal Tumorigenesis"*Cell*, 61:759–767 (1990).

Weiss, P., et al., "A Model of Growth & Growth Control in Mathematical Terms", *J. Gen. Physiol.*, 41(1):1–47 (1957).

Boukamp, P. et al., "Evironmental Modulation of the Expression of Differentiation . . . Carcinoma Cell Lines", *Cancer Research*, 45:5582–5592 (1985).

Trotter, N. L., "The Effect of Partial Hepatectomy on Subcutaneously Transplanted Hepatomas in Mice", *Cancer Research*, 21:778–782 (1961).

Rheinwald, J. G., "Serial Cultivation of Normal Human Epidermal Keratinocytes", *Methods in Cell Biology*, 21A:229–254 (1980).

Murata, M., et al., "Erythroid differentiation factor is encoded by the same mRNA as that of the inhibin Beta$_A$ chain", *Proc. Natl. Acad. Sci USA*, 85:2434–2438 (1988).

Thompson, N. L., et al., "Expression of Transforming Growth Factor–Beta1 in Specific . . . Neonatal Mice", *J. of Cell. Biol.*, 108:661–669 (1989).

Pelton, R. W., et al., "Expression of transforming growth factor Beta2 RNA during murine embryogenesis", *Development*, 106:759–767 (1989).

Mathews L. S., et al., "Expression Cloning of an Activin Receptor, a Predicted Transmembrane Serine Kinase", *Cell*, 65:973–982 (1991).

Weinstein, G. D., et al., "Fraction of labelled mitoses studies in normal and psoriatic skin" In: Psoriasis Cell Proliferation, Eds. Wright, N. et al., pp. 34–44 (1983).

Pinkus, H., "Examination of the Epidermis by the Strip Method of Removing horny layers", *J. of Invest. Derm.*, 383–386 (1951).

Abercrombie, M., "Localized formation of new tissue in an adult mammal" *Dept. of Anatomy & Embryology*, Univ. College, London Symposium Soc. Exp. Biol. 11:235–254 (1957).

Burns, E. R., "On the Failure of Self-Inhibition of Growth in Tumors" *Growth*, 33:25–45 (1969).

Yu, J., et al., "Importance of FSH-Releasing protein and inhibin in erythrodifferentiation", *Nature*, 330:765–767 (1987).

Cairns, J., "Mutation selection and the natural history of cancer" *Nature*, 255:197–201 (1975).

FIG. 1

Partial sequence of Guinea-pig Activin ßA.

5'
    CCC-TCT-GGC-TAC-CAC-GCC-AAC-TAC-TGT-GAG-GGT-
    GAG-TGC-CCC-AGC-CAC-ATA-GCA-GGC-ACC-TCG-GGC-
    TCC-TCA-CTT-TCT-TTC-CAC-TCA-ACG-GTC-ATC-AAC

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CCCTCTGGCT ACCACGCCAA CTACTGTGAG GGTGAGTGCC CCAGCCACAT AGCAGGCACC        60

TCGGGCTCCT CACTTTCTTT CCACTCAACG GTCATCAAC                              99
```

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GGNYNGARTG YGAYGG                                                       16
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
TGGVANGAYT GGATHRTNGC                                                   20
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid -continued (C) STRANDEDNESS: single
(D) TOPOLOGY: linear (ii) MOLECULE TYPE: cDNA (xi) SEQUENCE DESCRIPTION: SEQ ID NO:4:

RCANCCRCAY TCYTCNACDA T    21

(2) INFORMATION FOR SEQ ID NO:5:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

AGATCTGATA TCATCGATGA ATTCTTTTTT TTTTTTTTT T    41

TREATMENT OF HYPERPROLIFERATIVE EPIDERMAL CONDITIONS WITH ACTIVIN A

BACKGROUND OF THE INVENTION

Constant cell renewal in epithelial tissues is accomplished by a carefully balanced process in which new cells are constantly being produced in exact measure to the number of cells that are lost through cell death. Following wounding, a burst of mitotic activity takes place so that the number of cells produced outnumbers the cells that are dying. As the tissue mass is being replenished, mitotic activity slows so that eventually a new equilibrium between cell production and cell loss is obtained. Although it is clear that such process requires both positive and negative growth factors, the molecules involved in controlling epidermal homeostasis have not yet been characterized (Choi, Y. and Fuchs, E., *Cell Regulation,* 1:791–809 (1990)). Transforming growth factors of the β type (TGFβ)s are candidates to be major regulators in this process since it has been shown that both TGF-β1 and TGF-β2 can inhibit epidermal proliferation at ng/ml concentrations (Choi, Y. and Fuchs, E., *Cell Regulation,* 1:791–809 (1990)). TGF-β1 messenger RNAs are expressed in terminally differentiating epidermal cells in vivo (Thomson, N. L., Flanders, K. C., Smith, J. M., Ellingsworth, L. R., Roberts, A. B. and Sporn, M. B., *J. Cell. Biol.,* 108:661–669 (1989)). Furthermore, TGF-β2 and the TGF-β-related gene, Vgrl, are expressed at the time that stratification and keratinization in developing mouse epidermis take place (Lyons, R. M., Graycar, J. L., Lee, A., Hashmi, S., Lindquist, P. B. Chen, E. Y., Hogan, B. L. M. and Drynick, R., *Proc. Natl. Acad Sci. USA* 86: 4554–4558 (1989); Lyons, K. M., Pelton, R. W. and Hogan, B. L., *Development* 106:759–767 (1988). In spite of this it is not yet clear whether TGF-βs are major regulators of epidermal homeostasis. TGF-βs form part of a large family of molecules and although at first sight it appears that one factor can mimic the action of others, subtle differences often confer specificity and potentiation to different factors in different systems.

A feedback control is involved in epidermal homeostasis. Feedback control of epidermal cell proliferation is suggested by simple evidence. For example, under stress conditions the tissue never disappears although the mitotic activity is considerably depressed. Vice versa, psoriatic epidermis showing an abnormally high proliferative activity does not become thicker and thicker but reaches a homeostatic equilibrium.

This control is not due to contact inhibition. If keratinized or keratinizing cells are removed, for example by means of stripping with adhesive tape (Pinkus, H. J., *Invest. Dermatol.* 16:383–386 (1951)) or by friction, the underlying basal cells respond by a burst of mitotic activity so that the cell loss is rapidly and locally compensated. It should be noted that even though the basal layer was not altered in this experiment there was a burst of mitotic activity suggesting that contact inhibition is unlikely to be involved in the growth control mechanism of normal epidermis. As in the case of a deeper wound, the enhanced cell proliferation was—apart from a period of overshooting—automatically reduced to its normal value when the repair had been finished.

From this it is obvious that experiments on wound healing and tissue repair can provide insight into the regulatory mechanisms governing epidermal cell proliferation, although the repair of skin lesions is a highly complex process including primarily epithelial cell migration as well as division of epidermal cells and a response of the underlying connective tissue.

In order to provoke the repair process, Bullough and Laurence (Bullough, W. S. and Laurence, E. B. *Proc. Roy. Soc. B.* 151:517–536 (1960)), made a 1 cm long cut in the dorsal skin of mice which extended down through the panniculus carnosus. This resulted in a stimulation of mitotic activity which reached a peak after 36–48 h. This enhanced proliferative response was almost completely restricted to a zone with a width of 1 mm from the cut edge. Within this zone a gradient of mitotic activity with the highest activity proximal to the wound edge could be observed.

Feedback mitotic control in epidermis appears to be due to the presence of negative growth factors. In a second series of experiments said authors investigated the influence of a small cut made through the epidermis on one side of a mouse ear on the mitotic activity of the epidermis on the opposite side of the ear. A mouse ear is only about 0.15 mm thick and its two epidermal layers are separated by a very thin layer of connective tissue. It could be expected, therefore, that the zone of high mitotic activity adjacent to the wound would extend to the uninjured opposite side of the ear. Indeed, it was observed that the opposite undamaged epidermis showed a mitotic response which was as powerful as that adjacent to the wound. With proper control experiments, this effect was shown not to be due to the greatly enriched blood supply around the damaged area. The authors were thus left with the conclusion that the enhanced mitotic activity in the vicinity of the wound as well as on the opposite side of the ear was the consequence of either the production of a mitogenic agent (wound hormone, (Abercrombie, M., *Symposium Soc. Exp. Biol.* 11:235 (1957)) or the loss of an endogenous inhibitor which is synthesized within the skin.

Bullough and Laurence (Bullough, W. S. and Laurence, E. B. *Proc. Roy. Soc. B.* 151:517–536 (1960)) made a wound in the subcutaneous tissue including hair roots without damaging the overlying epidermis. Under these conditions no significant mitotic response of the epidermis was observed (though the wounded area developed a rich blood supply and suffered a heavy invasion of leucocytes). If the wound was not only a simple cut but a more extended lesion, the highest mitotic activity on the undamaged opposite side was found opposite to the center of the lesion. The authors considered this observation not to be consistent with the assumption of a wound hormone thought to be released from the wound edges but took it as strong evidence for the loss of a pre-existing mitotic inhibitor. They thus proposed that normally an inhibitory substance is in constant production, and that it may be lost partly with the cornified cells which are shed from the surface and partly by diffusion into the dermis. It may also be unstable. In the neighborhood of a wound there appears to be both a reduced inhibitor production and a drainage away of inhibitor into the wound (Bullough, W. S. and Laurence, E. B. *Proc. Roy. Soc. B.* 151:517–536 (1960)). Iversen et al. (Iversen, O. H., Bhangoo, K. S. and Hansen, K., *Virch. Arch. B.* 16:157–159 (1974)) repeated and extended this type of experiment on wound healing in an impressive study using the web membrane of the African fruit bat. Since this tissue resembles a mouse ear in many aspects (the two epidermal layers are separated by a thin connective tissue sheet with a diameter of 1 mm or less) but is much larger and easier to handle, it was found to be an almost ideal object for the purpose envisaged.

When an area of epidermis was removed from the ventral side of the web by stripping with adhesive tape, several waves of increased mitotic activity and the development of epidermal hyperplasia were observed adjacent to the wound as well as on the central region of the undamaged opposite side. Furthermore, retransplantation of the epidermis to the stripped area (which in fact should have increased the sources of putative wound hormone) prevented development of hyperplasia opposite the wound.

Hyperproliferative epidermal conditions.

There have been many studies attempting to describe and quantify the cell proliferation patterns of normal and diseased skin. Normal epidermis has a very low mitotic activity with cells cycling every 200–300 hours. Yet when the epidermis is wounded a burst of mitotic activity takes place so that the cells divide up to ten times faster depending on the conditions and the severity of the wound (Pinkus, H. J., *Invest. Dermatol.* 16:383–386 (1951); Bullough, W. S. and Laurence, E. B. *Proc. Roy. Soc. B.* 151: 517–536 (1960)). In contrast, human hair root cells are rapidly proliferating cells with cell cycle times in the order of 35 hours. Whilst the data on psoriatic epidermis is more controversial there is general agreement that psoriasis is a disease characterized by epidermal cell hyperproliferation and incomplete keratinization (Weinstein, G. D., Colton, A. and McCulloh, J. L., In: *Psoriasis Cell Proliferation*. Eds. Wright, N., Camplejohn, R. S. Churchill Livingstone (1983)). Estimation of cell cycle times for psoriasis vary from group to group and depend on the methods used. Weinstein et al. have conducted a study of normal and psoriatic epidermis in vivo using the frequency of labeled mitosis method and have reported that whilst the cell cycle time of normal skin is about 300 hours, involved psoriatic epidermal cells have a cell cycle time of about 37 hours (Weinstein, G. D., Colton, A. and McCulloh, J. L., *In: Psoriasis Cell Proliferation*. Eds. Wright, N., Camplejohn, R. S. Churchill Livingstone (1983)).

The accessibility of cutaneous and genital epithelial tumors has permitted use of the fraction of labeled mitosis (FLM) method to study cell kinetics in these tissues. In basal cell carcinoma and in squamous cell carcinoma kinetic data have been obtained which show kinetic parameters comparable to those of hyperproliferative skin conditions. However, a second peak in the FLM curves (which would have given a direct estimation of the cell cycle times), has not been reported.

Members of the TGF-$\beta$ superfamily induce differentiation in several tissues.

There is accumulating evidence that TGF-$\beta$-related genes are important regulators of many morphogenetic events. TGF-$\beta$1, $\beta$2 and $\beta$3 have been implicated in murine embryogenesis. Another group of the TGF-$\beta$ family whose members show greatest homology to the drosophila gene DPP and the Xenopus gene Vg1 includes Bone Morphogenetic proteins (BMP) (Thomson, N. L., Flanders, K. C., Smith, J. M., Ellingsworth, L. R., Roberts, A. B., and Sporn, M. B., *J. Cell Biol.*, 108: 661–669 (1989); Lyons, R. M., Graycar, J. L., Lee, A., Hashmi, S., Lindquist, P. B. Chen, E. Y., Hogan, B. L. M. and Drynick, R., *Proc. Natl. Acad. Sci. USA* 86:4554–4558 (1989)) (osteogenin), and 2b (now known as BMP-4) as well as the murine Vgrl, osteogenic protein 1, and GDF-1 (Jones, M. C., Lyons, K. M. and Hogan, B. L. M., *Development* 111:531542 (1991)). Another subgroup of the TGF-$\beta$-related molecules are the activins. The activins were initially found to elicit FSH release (Mason, A. J., Hayflick, J. S., Ling, N., Esch F., Ueno, N., Ying, S. Guillemin, R., Niall, H. and Seeburg, P. H., *Nature,* 318: 659–663 (1985); Vale, W., Rivier, J., Vaughan, J., McClintock, R., Corrigan, A., Woo, W. Karr, D. and Spiess, J., *Nature* 321:776–779 (1986); Ling, N., Ying, S. Y., Ueno, N., Shimasaki, S., Esch F., Hotta, M. and Guillemin, R., *Nature* 321:779–782 (1986)). Two forms of activins have been isolated and shown to be either disulfide-linked homodimer of the inhibin $\beta$A subunit (activin-A) or a heterodimer composed of a $\beta$A and a $\beta$B subunit (activin AB) (Mason, A. J., Hayflick, J. S., Ling, N., Esch F., Ueno, N., Ying, S. Guillemin, R., Niall, H. and Seeburg, P. H., *Nature,* 318:659–663 (1985); Vale, W., Rivier, J., Vaughan, J., McClintock, R., Corrigan, A., Woo, W. Karr, D. and Spiess, J., *Nature* 321:776–779 (1986); Ling, N., Ying, S. Y., Ueno, N., Shimasaki, S., Esch F., Hotta, M. and Guillemin, R., *Nature* 321:779–782 (1986)). Activin A has also been found to stimulate erythroid differentiation (Yu, J., Shao, L., Lemas, V., Yu, A. L., Vaughan, J., Rivier, J. and Vale, W. *Nature* 330:765–767 (1987)) and to promote neuron survival in vivo (Schubert, D., Kimura, H., LaCorbiere, M., Vaughan, J., Karr, D. and Fisher, W. H., *Nature* 344:868–870 (1990)). Activins, both A and B, have now been shown to induce the formation of mesodermal structures in Xenopus and chicks (Asashima, M., Nakano, H., Shimade, K., Kinoshita, K., Ishii, K., Shibai, H. and Ueno, N., *Roux's Arch. Dev. Biol.* 198:330–335 (1990); Smith, J. C. M., Price, B. M. J., Van Nimmen, K. and Huylecroeck, D. *Nature* 345:729–731 (1990); Thomsen, G., Woolf, T., Whitman, M., Sokol, S., Vaughan, J., Vale, W. and Melton, D.C. *Cell* 63:485–493 (1990); Mitrani, E. and Shimoni, Y., *Science* 247:1092–1094 (1990); Mitrani, E., Ziv., T., Thomsen, G., Shimoni, Y., Melton D. A., and Bril. A., *Cell* 63:495–501 (1990)).

Recently, the activins have been found to have strong differentiation capacities on embryonic primary ectodermal cells (Asashima, M., Nakano, H., Shimade, K., Kinoshita, K., Ishii, K., Shibai, H. and Ueno, N., *Roux's Arch. Dev. Biol.* 198:330–335 (1990); Smith, J. C. M., Price, B. M. J., Van Nimmen, K. and Huylecroeck, D. *Nature* 345:729–731 (1990)). Activin A can induce axial mesoderm in Xenopus and our group has shown that activin B is probably the endogenous inductor of axial structures in birds (Mitrani, E., Ziv., T., Thomsen, G., Shimoni, Y., Melton D. A., and Bril. A., *Cell* 63:495–501 (1990)). Also very recently Mathews and Vale (1991) reported the cloning of the activin receptor. This receptor seems to have common features with other growth factor receptors but in contrast to others it is the first receptor to display serine kinase activity (Mathews, L. S., Vale, W. W. *Cell* 65: 973–982 (1991)).

Tumor Suppressor Genes are involved in the control of cell proliferation.

Tumor formation arises as a consequence of alterations in the control of cell proliferation and disorders in the interactions between cells and their surroundings that result in invasion and metastasis. A breakdown in the relationship between increase in cell number resulting from cell division and withdrawal from the cell cycle due to differentiation or cell death lead to disturbances in the control of cell proliferation. In normal tissues, homeostasis is maintained by ensuring that as each stem cell divides only one of the two daughters remains in the stem cell compartment, while the other is committed to a pathway of differentiation (Cairns, J., *Nature* 255:197-200 (1975)). The control of cell multiplication will therefore be the consequence of signals affecting these processes. These signals may be either positive or negative, and the acquisition of tumorigenicity results form genetic changes that affect these control points.

It has now been possible to characterize some of these control points and to identify the genetic changes that contribute to malignancy. In the best-studied examples, changes at several different genes have been shown to occur within each tumor. These alterations affect genes concerned with positive stimuli to growth and genes whose products are normally involved in inhibition of cell growth (reviewed in Fearon, E. R. and Vogelstein, B., *Cell* 61:759-767 (1990)).

Tumors have a defined pattern of growth.

The patterns of growth of a variety of rapidly growing, transplantable and malignant tumors of epithelial origin are not random conglomerations of cells but organized tissues with characteristic histological patterns. The establishment of the basic pattern depends, first, on the connective-tissue-adjacent position of the mitotic cells, and second, on the distal movement, aging and finally death of the differentiated cells. In any tumor these normal rules persist. When growth begins a solid tumor typically consists of an outer sheath of connective-tissue-adjacent mitotic cells, a medial sheath of differentiated aging cells and an inner mass of dead cells. Except that the tumor forms a cyst instead of a sheet, the cells are stratified as they are, for instance, in the epidermis. The picture presented by a typical solid tumor is consistent with a situation in which there is an excessive number of mitotic-cycle cells and an inadequate number of post-mitotic aging cells. Thus, cell production continues to exceed cell loss.

Removal of one tumor accelerates growth of a second identical tumor.

When two identical tumors are present, the removal of one accelerates the growth of the other (Goodman, G. J., *Proc. Amer. Assoc. Cancer Res.* 2:207- (1957)); partial hepatectomy stimulates the growth of adenomatous hepatic nodules (Trotter, N. L., *Cancer Res.* 21:778 (1961)). When two tumors of different tissue origins are present together in the same animal, they grow independently of each other so that each reaches its usual plateau as if the other was not present (Burns, E. R., *Growth* 33:25 (1969)). This last experiment neatly disproves the idea that tumor growth is inhibited by nutrient exhaustion or by toxic metabolic products.

The most extensive studies of the plateau phenomenon in tumors are those of Bichel (Bichel, P., *Eur. J. Cancer* 6:291 (1970); Bichel, P. *Eur. J. Cancer* 8:167 (1972); Bichel, P., *Nat. Cancer Inst. Mon.* 38:197 (1973)), who carefully plotted the growth characteristics of three mouse ascites tumors, each derived from a different tissue and each reaching a stable plateau without killing its host. He found that the removal of tumor cells in the plateau phase causes the immediate resumption of growth of the remaining cell mass; that the cell-free ascites fluid, taken at the plateau phase and injected into another mouse, inhibits mitotic activity in tumor cells in the rapid growth phase, but only if these tumor cells are of the same type of tumor; that when two different tumors are grown simultaneously in the same mouse, each grows at its normal rate to reach its normal plateau irrespective of the presence of the other; and that, when two tumors are grown simultaneously in the same mouse, the cell-free ascites fluid from another mouse containing only one of the tumors inhibits the growth of only the same type of tumor leaving the other tumor to continue its uninhibited growth.

Activin A, and the gene encoding therefor, are known, inter alia, from European Patent Application No. 222,491. This publication discloses the synthesis of Activin A by recombinant techniques and its use in the manipulation of fertility in animals.

SUMMARY OF THE INVENTION

The invention relates to pharmaceutical preparations for the treatment of hyperproliferative epidermal conditions comprising as an active ingredient activin A or a biologically active essential fragment thereof, in a pharmaceutically acceptable carrier or diluent. The invention also relates to methods of treating hyperproliferative epidermal conditions by use of the pharmaceutical preparations of the invention. The preparations of the present invention are mainly intended for topical or subcutaneous application.

More particularly, the pharmaceutical preparations of the invention are intended for the treatment of hyperplastic epidermal conditions, such as psoriasis, or for inhibition of hair growth, and for the treatment of neoplastic epidermal conditions such as those characterized by a high proliferization rate for various skin cancers, for example basal cell carcinoma and squamous cell carcinoma.

BRIEF DESCRIPTION OF THE FIGURES

FIG. 1 shows the DNA sequence of a cloned fragment coding for guinea-pig activin $\beta$A chain (SEQ ID NO:1).

FIG. 2 shows that activin $\beta$A RNA is expressed in normal but not in transformed keratinocytes. Normal blot analysis of RNA derived from human foreskin keratinocytes growth in culture for 21 days (lane 2) and of RNA derived form a transformed cell line of epidermal origin SCL-1 (lane 1). 20 $\mu$g of total RNA were loaded onto each lane. The cloned DNA fragment was used as template to prepare antisense RNA probe to the human activin $\beta$A chain. A) Two major transcripts are detected at 2.8 and 3.4 kb. B) 28s band to illustrate the amount of RNA loaded on the gel.

DETAILED DESCRIPTION OF THE INVENTION

Figure 3A:
FIGS. 3A-3D depict the in situ hybridization of activin $\beta$A RNA in human skin. Frozen cryostat 8 $\mu$m sections from normal human skin hybridized to antisense DNA probe to activin $\beta$A chain (A and C) and to a sense probe (B and D) using HKA as template. In A and C, a strong hybridization signal can be detected throughout the whole epidermis but becomes stronger towards the basal layer. The signal in the dermis is considerably weaker (A and C). A and B, dark field at ×60 mag. C and D, normal light microscopy at ×120 mag.

The invention relates to pharmaceutical preparations for the treatment of hyperproliferative epidermal conditions comprising as active ingredient activin A or a biologically active essential fragment thereof, in a pharmaceutically acceptable carrier or diluent. The invention also relates to methods of treating hyperproliferative epidermal conditions by use of the pharmaceutical preparations of the invention.

More particularly, the pharmaceutical preparations of the invention are intended for the treatment of hyperplastic epidermal conditions, such as psoriasis, or for inhibition of hair growth, and for the treatment of neoplastic epidermal conditions such as those characterized by a high proliferization rate for various skin cancers, for example basal cell carcinoma and squamous cell carcinoma. The theoretical necessity for growth inhibitors as factors necessary for the control of epithelial homeostasis has long been postulated (Bullough, W. S. and Laurence, E. B. *Proc. Roy. Soc. B.* 151:517–536 (1960); Weiss, P. and Kavanau, J. L., *J. Phisiol.* 41:1–47 (1957)). There is strong evidence for negative growth factors as key regulators in this process. Yet the nature of the molecules involved has not been fully identified. TGF-β-related factors have been considered good candidates to act as differentiation and/or mitotic inhibitors at the cell-cell interaction level in epithelial tissues. As will be shown in the Examples hereafter, activin A mRNA is shown to be present in human keratinocytes grown in culture. In situ hybridization experiments indicate that in normal human skin, activin A mRNA expression is distributed throughout the epidermis but becomes stronger towards the basal layer. It will also be shown that following treatment with activin A containing medium (ACM), skin organ cultures show a decrease of thymidine incorporation in the epidermis. These results suggest that activin A may be directly involved in the control of growth and differentiation of epidermal tissues.

The results of the experiments presented in the Examples clearly indicate that treatment of various hyperproliferative epidermal conditions can diminish the proliferation rate of epidermal cells.

The present inventors have also found that activin A can inhibit proliferation of transformed epidermal cells such as SCL-1 (Boukamp, P., Thomas H., Rupniak, R. and Fusening, N., *Cancer Res.* 45:5582–5592 (1985)) cells growth in culture. The preparations of the present invention can thus also be employed in the treatment of neoplastic epidermal conditions.

It should be borne in mind that although other growth factors, even closely related ones, may also be expressed in the epidermis, each factor probably acts in a very specific manner. For instance, the inventors have not detected the closely related molecule activin-B in epidermis. Yet preliminary data suggest that activin-B is expressed in other types of epithelia where activin-A is absent. TGF-β although also expressed in normal epidermis is, in contrast to activin-A, expressed also in SCL-1 cells.

The preparations of the present invention are mainly intended for topical or subcutaneous application. Preferably, the preparations are in the form of an aqueous gel, water-dispersible lotion, or other pharmaceutically acceptable carriers, in the form of paste, tape or film support, or subcutaneous implants, preferably for the sustained release of the active ingredient. The preparations can also be in the form of sprays.

The biologically active ingredient is contained in the preparations in a suitable biologically effective amount, in the range of 3 to 300 ng per gram preparation. Higher or lower amounts might also be effectively employed.

The pharmaceutically acceptable carrier should be substantially inert, so as not to act with the active component. Suitable inert carriers include water, alcohol polyethylene glycol, mineral oil or petroleum gel, propylene glycol and the like. Pharmaceutically acceptable materials which effectively carry drug through the skin may be useful components of the carrier.

Topical administration of the preparations of the present invention can be effected by applying an adequate amount to and onto the areas to be treated and immediately adjacent thereto. Treatment by topical application should be regular and can be once or more daily, as prescribed by the attending physician.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

The preparations of the present invention can be used, as stated above, for the inhibition of hair growth, and as such, are to be considered cosmetic compositions. Cosmetic compositions known in the art, preferably hypoallergic and pH controlled are especially preferred.

The invention also relates to methods of treating hyperproliferative epidermal conditions by applying to the affected skin area the pharmaceutical compositions of the invention.

The methods of the present invention are useful in treating hyperplastic epidermal conditions such as psoriasis, or for inhibition of hair growth.

The present methods are also be useful in treating neoplastic skin conditions, such as basal cell carcinoma or squamous cell carcinoma.

The invention will be described in more detail with reference to the figures and the following Examples.

EXAMPLES

Example 1

Activin-βA but not activin-βB can be amplified by PCR from guinea-pig and human epidermis.

PCR was performed initially on cDNA obtained by reverse transcribing mRNA from guinea-pig keratinocytes using primers A1 (SEQ ID NO:2) and P1 (SEQ ID NO:5). A small volume of the PCR reaction was reamplified using instead primers V1 (SEQ ID NO: 3) and A2 (SEQ ID NO: 4). The fragment obtained (GKA) was sequenced directly (Mitrani, E., Ziv., T., Thomsen, G., Shimoni, Y., Melton D. A., and Bril. A., *Cell* 63:495–501 (1990)) and found to be 100% identical at the amino acid level to human activin βA chain in the region sequenced and 90% identical at the DNA level (FIG. 1) (SEQ ID NO: 1). The same procedure was repeated using instead total RNA derived from normal human keratinocytes grown in culture for a period of three weeks. A 270 bp fragment (HKA) was obtained which, upon direct sequencing, showed 100% similarity to human activin βA chain at the DNA level. Even though the primers used to isolate the activin genes could also bind to the activin βB chain (Thomsen, G., Woolf, T., Whitman, M., Sokol, S., Vaughan, J., Vale, W. and Melton, D. C. *Cell* 63:485–493 (1990); Mitrani, E., Ziv., T., Thomsen, G., Shimoni, Y., Melton D. A., and Bril. A., *Cell* 63:495–501 (1990)), direct sequencing revealed only the single βA component. The detailed method is as follows:

RNA preparation.

Total RNA was prepared as described previously (Mitrani, E., Ziv., T., Thomsen, G., Shimoni, Y., Melton D. A., and Bril. A., *Cell* 63:495-501 (1990)). RNA was prepared from normal primary human and guinea pig keratinocytes grown in culture for different periods. In addition, RNA was prepared from the cell line SCL-1 of epidermal origin. Briefly, the cells were digested in proteinase K (200 µg/ml) at 45° C. for 45 minutes. The digest was extracted twice with phenol chloroform and precipitated in 0.3M sodium acetate and 2 volumes of ethanol.

Total nucleic acids were resuspended in 10 mM Tris. HCl/10 mM $MgCl_2$, and digested with DNAse I (10 µg/ml) for 30 minutes at 37° C. in the presence of RNAsin (Promega).

Reverse transcription.

About 1-2 µg of total RNA were precipitated, resuspended in 4 µl of $H_2O$, 4 µl of reverse transcription buffer (BRL), 1 µl of cloned MMLV reverse transcriptase (BRL 200 units/µl), 1 µl of oligo dT primer (1 µg/µl), and 2.5 mM dNTPs in 10 µ$h_2$o were added and the reaction was incubated at 37° C. for one hour. After this the reaction mixture was divided into 1-2 µl aliquots and stored at −70° C. until used directly in a PCR reaction.

Activin Dimers for PCR reactions.

Degenerate primers that encompass sequences coding for both activin chains βA and βB were created with a linker added at each end. The 5'-end primer (A1) has a BamH1 site. The 3'-end primer (A2) has an EcoR1 site. A1 was designed to target a region which is highly specific to the activin genes, as all other members of the TGF-β superfamily include extra amino acids in this region.

The primers used for the PCR reactions are as follows:

A1: 5'GG(AGCT) (TC) (AGCT)GA(AG)TG(TC)GA(TC)GG 3'(SEQ ID NO: 2)

V1: 5'TGG(CAG)A(AGCT)GA(TC)TGGAT(ATC) (GA)T(AGCT)GC 3'(SEQ ID NO: 3)

A2: 5'(AG)CA(AGCT)CC(AG)CA(TC)TC(TC)TC(AGCT)AC(AGT)AT 3'(SEQ ID NO: 4)

P1: 5'AGATCTGATATCATCGATGAATTCTTTTTTTTTTTTTTTTT3'(SEQ ID NO: 5)

PCR on whole cDNA populations.

PCR was performed as described previously (Mitrani, E., Ziv., T., Thomsen, G., Shimoni, Y., Melton D. A., and Bril. A., *Cell* 63:495-501 (1990)). For the first round 40 cycles each containing a denaturation step at 94° C. for 30 sec, annealing at 37° C. for 40 sec and elongation at 72° C. for 1 minute were performed. The second round of amplification was done for 35 cycles under the same conditions. The fragment was separated by electrophoresis and sequenced directly as described previously (Mitrani, E., ZiV., T., Thomsen, G., Shimoni, Y., Melton D. A., and Bril. A., *Cell* 63:495-501 (1990)). For each PCR reaction 0.2 µl of 10× Taq buffer (Promega), 1 µl of 10 mM dNTPs, 2 µl of primer mix containing about 1 µg of each primer and 12 µl of deionized water were mixed on ice. 2 µl of DNA template were then added to each tube. The reactions were performed in three steps: denaturation at 94° C. for 30 sec, annealing at 37° to 44° C. for 1 minute, and elongation at 72° C. for 1 minute. This cycle was repeated forty times using a PCR cycler (Ericomp USA).

Preparation of single stranded labeled DNA.

A small amount (1-5 ng) of gel purified template DNA was mixed with 2 µl of 10× Taq buffer (Promega), 40 µCi (3000 Ci/mmol) $^{32}$p dATP, 200 µM of dGTP, dCTP, dTTP, 2 units of Taq polymerase (Promega) and the required 3'-end primer at 10 nM in a 20 µl reaction. The reaction was performed for 30 cycles of linear amplification, denaturation (94° C. for 30 sec), annealing (50° C. for 1 min) and elongation (72° C. for 1 min). $6 \times 10^7$ DPM per ng of template are obtained by this method. Two separate probes were prepared from the chick activin βB. The first was prepared using primers V1 and A2 to prepare the template cAB. The second βB probe was prepared from a smaller fragment obtained by PCR amplification of cAB using primers V1 and B2.

Direct sequencing.

DNA was sequenced directly after gel purification using the technique described by Winship (Winship, P. R., *Nucleic Acids Research* 17:1266 (1989)). $^{32}$P-dATP was used as marker. Gels were covered with saranwrap, and exposed directly to film for 12-24 hours.

Example 2

Activin βA RNA is expressed in normal but not in transformed keratinocytes.

Figure 2:
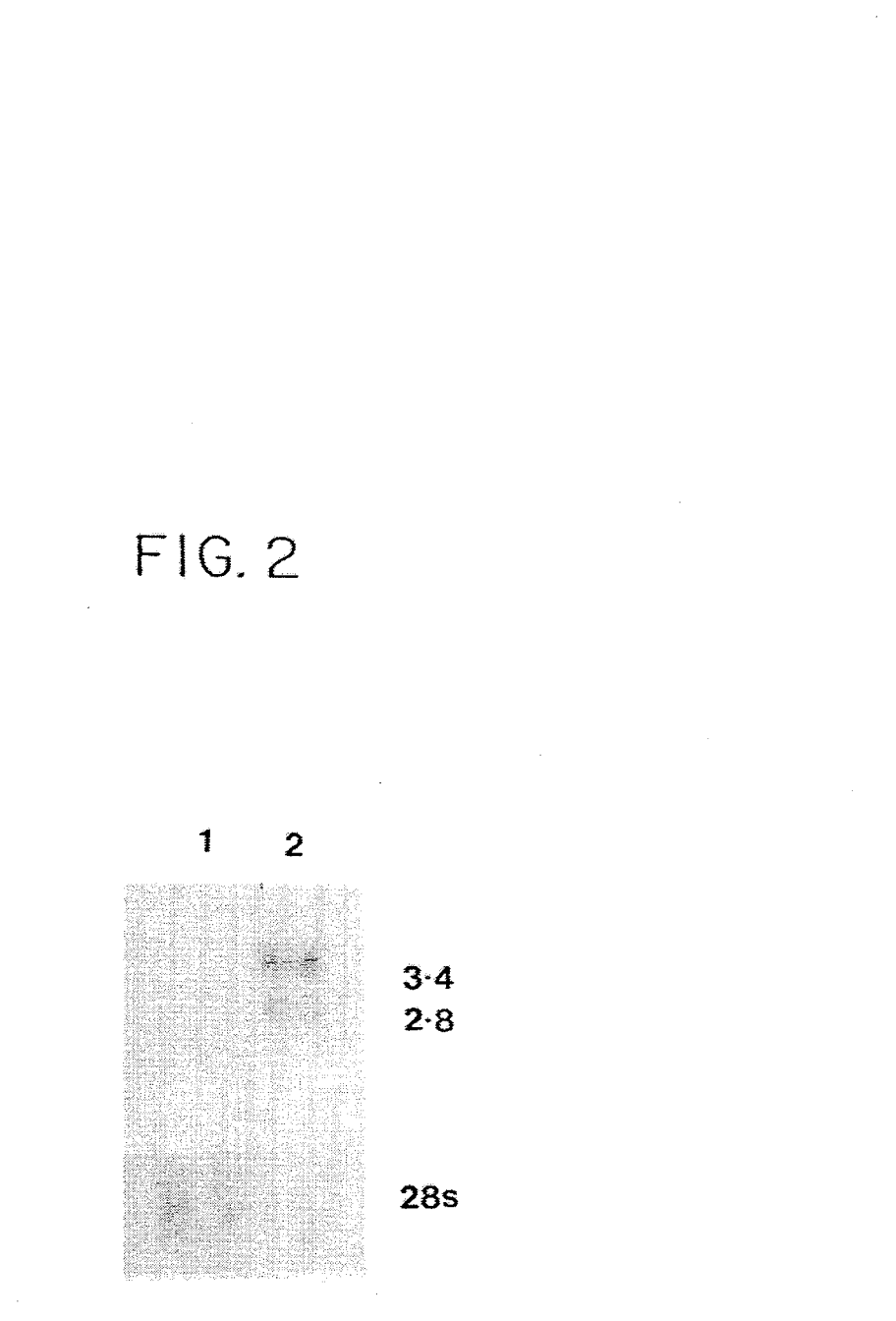

The human activin βA fragment HKA was used as template to prepare single stranded DNA and RNA antisense probes to be used in Northern blot analysis (Mitrani, E., Ziv., T., Thomsen, G., Shimoni, Y., Melton D.A., and Bril. A., *Cell* 63:495-501 (1990)). On RNA derived from cultures of normal differentiated human keratinocytes two transcripts of 3.4 and 2.8 kb in size (Albano, R. M., Godsave, S. F., Huylebroeck, D., Van Nimmen, K., Isaacs, H. V., Slack, J. M. W. and Smith, J. C., *Development* 110:435-443 (1990); Murata, M., Eto, Y. Shibai, Sakai, M. and Muamatsu, M., *Proc. Natl. Acad. Sci. USA* 85:2434-2438 (1988)), were readily seen (FIG. 2, lane 2). RNA was also prepared from a transformed line of epidermal origin SCL-1 (Boukamp, P., Thomas H., Rupniak, R. and Fusening, N., *Cancer Res.* 45: 5582-5592 (1985)), which, when hybridized to the activin-βA probe, gave no detectable signal (FIG. 2, lane 1).

The detailed method is as follows:

Northern blot analysis.

Northern blots were prepared as described previously (Mitrani, E., Ziv., T., Thomsen, G., Shimoni, Y., Melton D. A., and Bril. A., *Cell* 63:495-501 (1990)). Briefly, RNA was prepared as described above, denatured, electrophoresed on a 1% agarose/formaldehyde gel, transferred to a GeneScreen nylon membrane (Dupont) crosslinked with UV and hybridized to the different activin probes. Northern blots were reexamined using the RNA riboprobes. This allowed performing the hybridization conditions at higher stringency. For this case the blots were hybridized at 55° C. in 50% formamide. Washes were at 68° C. in 0.1×SSC and 0.1% SDS.

Example 3

Activin βA RNA is expressed in normal human epidermis.

Figure 3B:
Figure 3C:
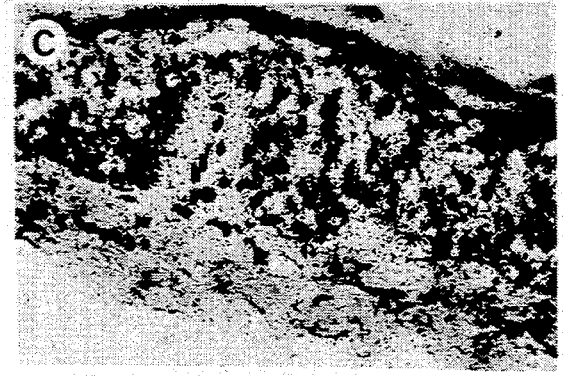
Figure 3D:

In situ hybridization experiments on normal human skin were performed as described (Rogers, M. and Zeller, R., *Current Protocols in Molecular Biology*, F. Ausbel, R. Brent, R. E. Kingston, D. Moore, J. Siedman, J. A., Smith and K. Struhl, Eds., John Wiley & Sons. Interscience, New York). A clear signal was observed in the sections hybridized with the HKA antisense probe. Hybridization could be observed throughout most of the epidermis up to the stratum granulosum, becoming stronger in the lower layers including the stratum basale (FIGS. 3a, 3c). No signal was detected with the sense probe (FIGS. 3b, 3d).

Hybridization conditions.

Hybridization solution contained: 50% formamide, 5×SSC, 1×Denhardts solution, 0.1 mg/ml Salmon sperm DNA and 1×10$^6$ dpm/ml of the p$^{32}$ labelled probe. Hybridization was at 42° C. Washes were 3 times, 20 minutes each with 50% formamide at 42° C.

Example 4

Activin inhibits proliferation of keratinocytes grown in culture.

Activin preparation.

Activin was prepared from conditioned medium from p388D1 cells as described previously (Thomsen, G., Woolf, T., Whitman, M., Sokol, S., Vaughan, J., Vale, W. and Melton, D.C. *Cell* 63:485–493 (1990)). Activin A was resuspended in water at 30 ng/ml and added directly to the culture medium. Activin was found to be effective at concentrations of 15 to 30 pM.

Results indicate that ACM inhibits proliferation of both guinea-pig (Dvir A., Milner, Y., Chomsky, O., Gilon, Ch., Gasit, A. and Levitsky, A., *J. Cell Biol.* (In press)) and human keratinocytes grown in culture on mitomycin-c-treated 3T3 feeder layers (Rheinwald, J. A., *Meth. in Cell. Biol.* 21A: 229–254 (1980); Green, H., Harvey Lectures series, 74, 101, 139 (1979)) (Table 1). ACM did not inhibit proliferation of normal 3T3 cells grown separately. Keratinocytes obtained by trypsinization were plated and grown in monolayer cultures as described previously (Dvir. A., Milner, Y., Chomsky, O., Gilon, Ch., Gasit, A. and Levitsky, A., *J. Cell Biol.* (In press); Rheinwald, J. A., *Meth. in Cell. Biol.* 21A: 229–254 (1980); Green, H., Harvey Lectures series, 74, 101, 139 (1979)).

TABLE 1

Effect of ACM on Thymidine Incorporation into Keratinocytes Grown in Monolayer Cultures

|  | Control DPM/10$^3$ cells | % | ACM DPM/10$^3$ cells | % |
|---|---|---|---|---|
| Human epidermis | 1330 | 100 | 585 | 44 |

Example 5

Activin inhibits proliferation of guinea-pig keratinocytes in skin organ culture.

Guinea-pig skin explants were grown in monolayer cultures in the presence or absence of activin containing medium (ACM). DNA synthesis, as measured by thymidine incorporation was significantly lower in the epidermis of ACM-treated skin explants than in control explants. In contrast, thymidine incorporation was significantly higher in the dermis of ACM-treated skin explants than in untreated controls (Table 2).

TABLE 2

Effect of ACM on Thymidine Incorporation into Guinea-Pig Epidermis Cells from Skin Organ Cultures

|  | Control DPM/mg | % | ACM DPM/mg | % |
|---|---|---|---|---|
| Guinea-Pig epidermis | 4668 | 100 | 3604 | 77 |
| n | 5 |  | 8 |  |

Example 6

Activin inhibits proliferation of human keratinocytes in skin organ cultures.

Human skin explants were grown in monolayer cultures in the presence or absence of activin containing medium (ACM). DNA synthesis, as measured by thymidine incorporation was significantly lower in the epidermis of ACM-treated skin explants than in control explants. In contrast, thymidine incorporation was significantly higher in the dermis of ACM-treated skin explants than in untreated controls (Table 3).

TABLE 3

Effect of ACM on Thymidine Incorporation into Human Epidermal Cells from Skin Organ Cultures

|  | Control DPM/mg | % | ACM DPM/mg | % |
|---|---|---|---|---|
| Human epidermis | 1419 | 100 | 926 | 65 |
| n | 6 |  | 7 |  |

Detailed methods for Examples 5 and 6:

In vitro skin organ cultures.

Both guinea-pig and human skin organ explants were grown in culture in the presence or absence of ACM. Results show thymidine incorporation as DPM/mg tissue, expressed also as percentage of untreated controls. n=No. of experiments. Ears from young (100–200 gr) guinea pigs were shaved with a scalpel and immersed 60 sec in 70% ethanol. Lower and upper skins were separated from the cartilage. Fat as well as excess dermal tissue were removed and the skin was cut into 0.5–1 cm$^2$ pieces. Similarly, human foreskins (24 hours post operation from individuals one to twenty years old) were rinsed in 70% ethanol, scraped with a scalpel on the external side and trimmed from supporting subdermal and some dermal tissue. All skin explants were grown under the same culture conditions. For each experiment skin explants were all derived from the same source and cultured, two explants per 35 mm petri dishes in 2 ml of DMEM containing 10% FCS, and 0.5 µg/ml hydrocortisone. ACM-treated dishes received in addition either 20% XTC-CM (Smith, J. C. M., Price, B. M. J., Van Nimmen, K. and Huylecroeck, D. *Nature* 345: 729–731 (1990)) or 0.5% PIF (Albano, R. M., Godsave, S. F., Huylebroeck, D., Van Nimmen, K., Isaacs, H. V., Slack, J. M. W. and Smith, J. C., *Development* 110:435–443 (1990)). Dishes were cultured for 24 to 96 hours at 37° C. and 5% CO$_2$ with gentle shaking. The culture medium was changed every 36 hours. 12–14 hours before termination of the experiment $^3$H-thymidine (Amersham, 5 µCi/ml, 80 Ci/mMole) was added to the cultures. Explants were then removed, washed with cold PBS and incubated in 2M CaCl$_2$ containing 10 mM non-labeled thymidine for 2 hours. The epidermis becomes loosened by this treatment and was removed as a sheet into Whatman paper for drying excess fluid. The dermal pieces were also dried this way and both tissue types were weighed and processed further. The tissues were then washed three times with agitation in 0.5% Triton X-100 solution containing 2 mM MgCl$_2$ and 10 mM thymidine to remove most (>95%) of the non-bound thymidine. Tissues were then incubated for 6 hours at 37° C. in 10 mM Tris pH 7.4, containing 1 mM MgCl$_2$, 0.1% Triton X-100 and 2 µg/ml DNAse (type I crystallized, Boehringer-Mannheim). Both the digesting solution and the digested tissues were counted in scintillation fluid. More than 90% of the $^3$H-thymidine was found to be removed from the tissues into the DNAse solution by this procedure. DNAse-solubilized counts were expressed per mg of tissue and shown as percentage of untreated controls.

Example 7

It has also been found that Activin A RNA is not expressed in SCL-1 cells, a transformed line of epidermal origin (see FIG. 2).

Example 8

Activin A can inhibit proliferation of SCL-1 cells grown in culture.

SCL-1 cells were grown in monolayer cultures in the presence or absence of ACM. DNA synthesis as measured by thymidine incorporation was significantly lower in ACM-treated cells than in control cells (Table 4). Cells were grown as described previously (Boukamp, P., Thomas H., Rupniak, R. and Fusening, N., *Cancer Res.* 45:5582–5592 (1985)).

TABLE 4

Effect of ACM on Thymidine Incorporation into Transformed Human Epidermal Cells SCL-1

|  | Control DPM/mg | % | ACM DPM/mg | % |
|---|---|---|---|---|
| Human SCL-1 cells | 972 | 100 | 715 | 71 |
| n | 6 |  | 6 |  |

Equivalents

Those skilled in the art will recognize, or be able to ascertain using no more than routine experimentation, many equivalents to the specific embodiment of the invention described herein. Such equivalents are intended to be encompassed by the following claims.

I claim:

1. A method of treating a hyperproliferative epidermal condition comprising applying to the affected skin area a pharmaceutical composition comprising as active ingredient a biologically effective amount of activin A in a pharmaceutically acceptable carrier.

2. A method according to claim 1 wherein the hyperproliferative epidermal condition is a hyperplastic epidermal condition.

3. A method according to claim 2 wherein the hyperplastic epidermal condition is psoriasis.

4. A method according to claim 1 wherein the hyperproliferative epidermal condition is a neoplastic epidermal condition.

5. A method according to claim 4 wherein the neoplastic epidermal condition is squamous cell carcinoma.

6. A method according to claim 4 wherein the neoplastic epidermal condition is a basal cell carcinoma.

* * * * *